(12) United States Patent
Henrio

(10) Patent No.: US 6,448,314 B1
(45) Date of Patent: Sep. 10, 2002

(54) USE OF MONOHYDRATE ZINC ACETYLACETONATE AS HALOGENATED POLYMER STABILIZER AND PREPARATION METHOD

(75) Inventor: Francoise Henrio, Monteleger (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/623,989

(22) PCT Filed: Mar. 12, 1999

(86) PCT No.: PCT/FR99/00568

§ 371 (c)(1),
(2), (4) Date: Nov. 17, 2000

(87) PCT Pub. No.: WO99/46322

PCT Pub. Date: Sep. 16, 1999

(51) Int. Cl.[7] .......................... C08K 5/06; C08K 15/09; C07F 3/06

(52) U.S. Cl. ................ 524/108; 524/357; 524/396; 524/567; 556/40; 556/121; 556/122; 556/131; 556/133

(58) Field of Search .............. 252/400.53, 389.53; 524/108, 357, 396, 567; 556/40, 121, 122, 131, 133

(56) References Cited

U.S. PATENT DOCUMENTS

| | | | | |
|---|---|---|---|---|
| 3,474,464 A | * | 10/1969 | Matthews et al. | |
| 3,492,267 A | * | 1/1970 | Wood | |
| 3,860,568 A | * | 1/1975 | Chabert et al. | |
| 3,965,068 A | * | 6/1976 | Dickens, Jr. | |
| 4,048,035 A | * | 9/1977 | Ide et al. | |
| 5,206,341 A | * | 4/1993 | Ibay et al. | 528/361 |
| 5,534,566 A | * | 7/1996 | Wehner et al. | 524/27 |
| 5,641,350 A | * | 6/1997 | Chassot et al. | 106/493 |
| 5,885,919 A | * | 3/1999 | Bortinger | 502/209 |

FOREIGN PATENT DOCUMENTS

| | | |
|---|---|---|
| FR | 1 524 717 | 9/1967 |
| FR | 1 576 711 | 1/1969 |
| WO | 97 40094 | 10/1997 |
| WO | WO 97/40094 | * 10/1997 |

* cited by examiner

*Primary Examiner*—Joseph D. Anthony
(74) *Attorney, Agent, or Firm*—Burns, Doane, Swecker & Mathis, L.L.P.

(57) ABSTRACT

The subject of the present invention is the use of zinc ateylacetonate comprising at least 4.4% by weight of water as halogenated polymer stabilizer.

Its subject is likewise a process for the preparation of zinc acetylacetonate monohydrate, in which a zinc oxide and/or hydroxide and acetylacetone are brought into contact, in the presence of a solvent; the said solvent being used with a quantity of between 20 and 200 parts by weight, per 100 parts by weight of acetylacetone.

11 Claims, No Drawings

USE OF MONOHYDRATE ZINC ACETYLACETONATE AS HALOGENATED POLYMER STABILIZER AND PREPARATION METHOD

The subject of the present invention is the use of zinc acetylacetonate, predominantly crystallized in the form of a monohydrate compound, as stabilizing agent for halogenated polymers.

Its subject is likewise a process for the preparation of the said zinc acetylacetonate.

Anhydrous zinc acetylacetonate is a product known in the literature, as well as its role of stabilizing halogenated polymers, and most particularly chlorinated polymers, such as poly(vinyl chloride).

However, while the importance of this compound is not under challenge, it exhibits, nevertheless, the disadvantage of having to be stored under special conditions, free of water. In the opposite case, under the effect of ambient humidity, the product cakes and can no longer be used as it is.

The aim of the present invention is to provide another type of zinc acetylacetonate which can be used as agent stabilizing halogenated polymers, not exhibiting the above disadvantage.

The first subject of the present invention is therefore the use of zinc acetylacetonate comprising at east 4.4% by weight of water, as halogenated polymer stabilizer.

It should be noted that for the sake of simplicity and of clarity of the disclosure which follows, the zinc acetylacetonate whose use constitutes one of the subjects of the invention, will be described as "monohydrate", to distinguish it from the "anhydrous" zinc acetylacetonette used up until now.

Likewise its subject is a process for the preparation of zinc acetylacetonate monohydrate, in which a zinc oxide and/or hydroxide and acetylacetone are brought into contact, in the presence of a solvent; the said solvent being used with a quantity of between 20 and 200 parts by weight, per 100 parts by weight of acetylacetone.

It is important to specify that up until now, reference has only been made to zinc acetylacetonate in anhydrous form, as halogenated polymer stabilizer. It is indeed known in this field that the presence of water in these compositions should be as low as possible. Indeed, given the high temperatures for forming such formulations, the water is vaporized and, upon escaping, can cause the appearance of defects in the final article, which is obviously not desirable.

However, it has been found that zinc acetylacetonate monohydrate, contrary to what was expected, did not exhibit any disadvantage when it was introduced into a halogenated polymer formulation. Indeed, during the use of the composition thus additivated, the appearance of bubbles or other defects due to the evacuation of the water is not observed.

Furthermore, in the publication by E. Lippert and M. R. Truter, which appeared in Journal of Chemical Society, 1960, p. 4996–5006, it is indicated that the monohydrated form of zinc acetylacetonate is the most stable crystalline form. Persons skilled in the art would therefore have expected to have a lower stabilizing activity than the anhydrous compound. However, here again, nothing of the such was observed.

It should be noted finally that the monohydrate compound is stable over time and does not cake, even when it is stored under an ambient atmosphere, that is to say with some humidity.

However, other characteristics and advantages of the present invention will appear more clearly on reading the description which follows.

The composition used in the invention is therefore zinc acetylacetonate comprising at least 4.4% by weight of water.

More particularly, the water content is between 4.4 and 8.8% by weight. According to a particular variant of the invention, the composition used has a water content of between 4.75% and 8.15% by weight. According to an advantageous variant of the invention, the compound has a structure similar to that of zinc acetylacetonate monohydrate.

Expressed differently, the compound according to the invention corresponds to the following average formula:

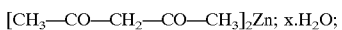

$$[CH_3-CO-CH_2-CO-CH_3]_2Zn; x.H_2O;$$

in which x is a number which is an integer or otherwise, greater than or equal to 0.65.

More particularly, the zinc acetylacetonate used in the invention is such that the abovementioned coefficient x is between 0.65 and 1.3. According to a more specific embodiment, the coefficient x is between 0.7 and 1.2.

Preferably, a compound which is predominantly crystallized in the form of a .monohydrate compound is used. In other words, the coefficient x is of the order of 1.

The crystals of zinc acetylacetonate hydrate according to the invention exhibit a limited acicular character (morphology different from that of a needle).

It should be noted that this product may exist in the form of a powder but also in a granulated or compacted form if necessary, subject to an appropriate forming step.

The zinc acetylacetonate may be obtained using conventional processes with or without solvent.

Reference may be made, for example, to the manual "Metal β-diketonates and allied derivatives" by R. C. Mehrota, R. Gaur, D. P. Gaur, which appeared in 1978, Academic Press, in which various methods for synthesizing these products are described.

A second subject of the present invention consists in another process which makes it possible to obtain zinc acetylacetonate hydrate.

This process consists in bringing a zinc oxide and/or hydroxide and acetylacetone into contact, in the presence of a solvent; the solvent being used in a quantity of between 20 and 200 parts by weight, per 100 parts by weight of acetylacetone.

Preferably, the content of solvent is less than or equal to 100 parts by weight relative to the same reference.

According to a more specific variant of the invention, the quantity of solvent used is at least 40 parts by weight relative to the same reference, and preferably at least 50 parts by weight.

Thus, one embodiment of the process according to the invention consists in using a quantity of solvent of between 20 and 100 parts by weight per 100 parts by weight of acetylacetone, more particularly between 40 and 100 parts by weight, and preferably between 50 and 100 parts by weight.

The solvent used in the reaction is more particularly a compound capable of solubilizing acetylacetone and it is preferably inert towards the constituents of the reaction mixture, under the reaction conditions.

According to a particularly advantageous variant of the present invention, the solvent is chosen from compounds whose boiling point is at most 100° C., measured at atmospheric pressure.

Among the compounds which can be used as solvents, there may be mentioned, with no limitation being intended, $C_1$–$C_6$ aliphatic alcohols such as methanol, ethanol or propanol. Also suitable are ketones, such as acetone; compounds comprising amide functions, such as formamide or dimethylformamide; compounds which are aromatic, such as benzene, or optionally comprising one or more alkyl substituents.

Obviously, using a combination of the solvents indicated above will not depart from the scope of the present invention.

The bringing into contact takes place, in addition, in the presence of an acetylacetone/zinc oxide and/or hydroxide molar ratio of between 2/1 and 2.4/1. Preferably, the process according to the invention is carried out in the presence of a molar ratio of between 2/1 and 2.2/1. According to a particularly advantageous variant of the present invention, the bringing into contact takes place with an acetylacetone/zinc oxide and/or hydroxide molar ratio close to the stoichiometric value.

The bringing into contact takes place with stirring.

Preferably, the reaction is carried out in a turbosphere-type reactor, or any other apparatus provided with mechanical stirring means allowing good homogenization of a heterogeneous reaction mixture.

According to a specific embodiment of the invention, the bringing into contact is carried out by introducing the acetylacetone into a zinc oxide and/or hydroxide and solvent mixture.

The bringing into contact of the reagents is carried out while the temperature is preferably maintained between room temperature and about 100° C. More particularly, the bringing into contact takes place at a temperature of less than 80° C. According to a preferred variant of the invention, the bringing of the acetylacetone into contact with the oxide and/or hydroxide is carried out at a temperature of less than or equal to the reflux temperature of the solvent used (or the solvent mixture).

The bringing into contact may be carried out under an inert atmosphere (such as nitrogen or a rare gas) or under air.

The duration of the operation is conventionally one hour to 4 hours.

Once the introduction has been carried out, the stirring and the temperature are preferably maintained for one to two hours.

After this preferred finishing step, the solvent is removed from the reaction mixture.

The procedure is preferably carried out by distillation.

An advantageous embodiment of the invention consists in carrying out the removal of the solvent in two successive steps. Thus, the first step takes place under atmospheric pressure, by uniformly increasing the temperature so as to distil the solvent without removing the water present. The second step takes place under reduced pressure so as to remove the remaining traces of solvent.

During this second step, the procedure is carried out such that the content of water in the zinc acetylacetonate hydrate obtained remains in the range indicated above.

It should be noted that the process according to the invention makes it possible to limit the acicular character of the crystals obtained, that is to say not to promote the growth of the crystals in the form of a needle. Without wishing to be limited by any theory, it has been observed that crystals exhibiting a pronounced acicular character had a greater ability to cake, or to flow less well.

At the end of the process according to the invention, a product is obtained in the form of a finely divided powder, which it can be envisaged to form, in particular by means of a granulation or compaction step.

The importance of the process according to the invention is that it makes it possible to cumulate, very advantageously, the advantages of the conventional processes without solvent and with solvent, without having the disadvantages thereof.

Indeed, the processes using solvents have the advantage of exerting a good control of the exothermicity of the reaction, but in return, they are not very productive. On the other hand, the processes without solvent are very productive but can cause difficulties for appropriately controlling the heat released during the reaction.

However, unpredictably, the process according to the invention is not only a productive process, but it also makes it possible to correctly control the heat of reaction.

As was indicated above, the zinc acetylacetonate monohydrate which has just been described is used as stabilizing agent for halogenated polymers, which are more particularly chlorinated polymers.

The zinc acetylacetonate monohydrate has an effect on the thermal stability of the polymer, but also on its stability towards light.

According to a specific characteristic of the invention, the content of zinc acetylacetonate monohydrate is more precisely between 0.01 and 2 g per 100 g of halogenated polymer. More particularly, the content of this compound is between 0.05 and 1 g in relation to the same reference.

The invention is particularly well suited to the stabilization of formulations based on poly(vinyl chloride) (PVC).

Poly(vinyl chloride) is understood to mean compositions whose polymer is a homopolymer of vinyl chloride. The homopolymer may be chemically modified, for example by chlorination.

Many copolymers of vinyl chloride can also be stabilized using the composition according to the invention. These are in particular polymers obtained by copolymerization of vinyl chloride with monomers having an ethylenically polymerizable bond, such as for example vinyl acetate, vinylidene chloride; maleic acid, fumaric acid or esters thereof; olefins such as ethylene, propylene, hexene; acrylic or methacrylic esters; styrene; vinyl ethers such as vinyl dodecyl ether.

Usually, the copolymers contain at least 50% by weight of vinyl chloride units and preferably at least 80% by weight of such units.

PVC alone or in a mixture with other polymers is the chlorinated polymer most widely used in the stabilized formulations according to the invention.

In general, any type of poly(vinyl chloride) is suitable, regardless of its mode of preparation. Thus, the polymers obtained, for example, using processes intermass, in suspension or in emulsion may be stabilized using the composition according to the invention, regardless of the intrinsic viscosity of the polymer.

The formulations may contain the stabilizing additives conventionally used in the field.

Thus, there may be mentioned the hydrochloric acid scavenging compounds which may be of the organic type or of the inorganic type, and may be present alone or in the form of mixtures Among the hydrochloric acid scavengers of the organic type, there may be mentioned more particularly the compounds comprising an alkaline-earth metal or a metal chosen from columns IIB, IIA and IVB of the periodic table of elements (which appeared in the supplement to Bulletin de la Société Chimique de France, no. 1, January 1966).

The cations are more particularly preferably chosen from calcium, barium, magnesium, strontium, zinc, cadmium, tin or lead.

It should be noted that it is possible to envisage combinations such as, for example, a mixture of hydrochloric acid scavenger based on calcium and zinc, barium and zinc, barium and cadmium, the first combination being preferred.

As regards the hydrochloric acid scavenger compounds of the organic type comprising at least one of the elements of columns IIB and IIA, there may be mentioned most particularly the salts of organic acids, such as aliphatic or aromatic carboxylic acids, or fatty acids, or aromatic alcoholates or phenolates.

The ones most commonly used are, for example, the salts of the IIA or IIB elements of maleic, acetic, diacetic, propionic, hexanoic, 2-ethylhexanoic, decanoic, undecanoic, lauric, myristic, palmitic, stearic, oleic, ricinoleic, behenic (docosanoic), hydroxystearic, hydroxyundecarioic, benzoic, phenylacetic, para-tert-butylbenzoic and salicylic acids, phenolates, alcoholates derived from naphthol or phenols substituted with one or more alkyl radicals, such as nonylphenols.

For practical reasons or for economic reasons there are preferably chosen among the abovementioned alkaline-earth metal organic compounds, alkaline-earth metal propionate, alkaline-earth metal oleate, alkaline-earth metal stearate, alkaline-earth metal laurate, alkaline-earth metal ricinolate, alkaline-earth metal docosanoate, alkaline-earth metal benzoate, alkaline-earth metal para-tert-butylbenzoate, alkaline-earth metal salicylate, alkaline-earth metal and mono(2-ethylhexyl) maleate, alkaline-earth metal nonylphenates, alkaline-earth metal naphthenate and among the abovementioned organic compounds of cadmium, cadmium propionate, cadmium 2-ethylhexanoate, cadmium laurate, cadmium stearate, cadmium salicylate, cadmium and mono(2-ethylhexyl) maleate, cadmium nonlyphenates and cadmium naphthenate.

As regards the organic-type compounds comprising lead, there may be mentioned in particular those described in ENCYCLOPEDIA of PVC by Leonard I. NASS (1976), page 299–303.

They are very diverse compounds of which the most commonly used are dibasic lead carbonate, tribasic lead sulphate, tetrabasic lead sulphate, dibasic lead phosphite, lead ortho-silicate, basic lead silicate, coprecipitate of lead silicate and sulphate, basic lead chlorosili.cate, coprecipitate of silica gel and of lead ortho-silicate, dibasic lead phthalate, neutral lead stearate, dibasic lead stearate, tetrabasic lead fumarate, dibasic lead maleate, lead 2-ethylhexanoate, lead laurate.

As regards the compounds based on tin, reference may be made in particular to the manual "PLASTICS ADDITIVES HANDBOOK" by GACHTER/MULLER (1985) pages 204–210 or in ENCYCLOPEDIA OF PVC by Leonard I. NASS (1976) pages 313–325.

They are more particularly mono- or di-alkyltin carboxylates and mono- or di-alkyltin mercaptides.

Among these compounds, those most commonly used are the derivatives of di-n-methyltin, di-n-butyltin or di-n-octyltin such as, for example, dibutyltin dilaurate, dibutyltin maleate, dibutyltin laurate-maleate, dibutyltin bis(mono-$C_4$–$C_8$-alkyl maleate), dibutyltin bis(lauryl-mercaptide), dibutyltin S-S'-(diisooctyl mercaptoacetate), dibutyltin β-mercaptopropionate, polymeric di-n-octyltin maleate, di-n-octyltin bis-S- S' (isooctyl mercaptoacetate), di-n-octyltin β-mercaptopropionate. The monoalkylated derivatives of the abovementioned compounds are also suitable.

As hydrochloric acid scavenger of the inorganic type, there may also be mentioned aluminium and/or magnesium sulphates and/or carbonates, in particular of the hydrotalcite type. It is recalled that the compounds of the hydrotalcite type correspond to the following formula: $Mg_{1-x}Al_x$ $(OH)_2A^{n-}_{x/n} \cdot mH_2O$, in which x is between 0 excluded and 0.5 $A^{n-}$ represents an anion such as carbonate in particular, n varies from 1 to 3 and m is positive.

It is also possible to use essentially amorphous compounds of formula $(MgO)_y, Al_2O_3, (CO_2)_x, (H_2O)_z$, in which x, y and z obey the following inequalities: $0<x\leq0.7$; $0<y\leq1.7$ and $z\geq3$. These compounds are in particular described in Patent Application EP 509 864. Moreover, the compounds called catoites of formula $Ca_3Al_2(OH)_{12}$ or $Ca_3Al_2(SiO)_4(OH)_{12}$ are suitable as hydrochloric acid scavenging compounds of the inorganic type.

All the hydrochloric acid scavengers of the inorganic type cited above are suitable for carrying out the invention.

The content of scavenger of the inorganic type mentioned above is more particularly between 0.1 and 10 g per 100 g of halogenated polymer. Preferably, this content is between 0.3 and 3 g in relation to the same reference. According to a still more specific embodiment of the invention, this content is between 0.3 and 1 g relative to 100 g of halogenated polymer.

The content of scavenger of the organic type is more particularly between 0.1 and 10 g per 100 g of halogenated polymer, preferably between 0.1 and 3 g relative to the same reference.

According to a first variant, there is used, in addition to the zinc acetylacetonate monohydrate, at least one hydrochloric acid scavenger, comprising at least one scavenger of the inorganic type and at least one scavenger of the organic type chosen from the calcium and/or zinc salts of carboxylic acids.

All the hydrochloric acid scavengers of the inorganic type cited above are suitable for carrying out the invention.

However, preferably, the scavenger of the inorganic type is chosen from the compounds of the following formula: $Mg_{1-x}Al_x$ $(OH)_2A^{n-}_{x/n} \cdot mH_2O$, in which x is between 0 excluded and 0.5, $A^{n-}$ represents an anion such as carbonate in particular, n varies from 1 to 3 and m is positive.

As regards the scavenger of the organic type, the composition according to this first variant comprises at least one scavenger based on calcium, optionally combined with a scavenger based on zinc.

The salts of aromatic or aliphatic carboxylic acids or the fatty acids indicated above are suitable for carrying out this first variant.

According to this first variant, the content of scavenger of the inorganic type mentioned above is more particularly between 0.1 and 10 g per 100 g of halogenated polymer. Preferably, this content is between 0.3 and 3 g in relation to the same reference. According to a still more specific embodiment of the invention, this content is between 0.3 and 1 g relative to 100 g of halogenated polymer.

The content of scavenger of the organic type defined for this first variant is more particularly between 0.1 and 4 g per 100 g of halogenated polymer, preferably between 0.3 and 2 g in relation to the same reference.

A second variant consists of a composition comprising, in addition to zinc acetylacetonate monohydrate, as hydrochloric acid scavenger, at least one organic scavenger chosen from the compounds based on lead.

Lead salts are more particularly used among those described above. However, according to a preferred embodiment, the lead salts used are chosen from lead phosphite combined with neutral or dibasic lead stearates, tri- or tetrabasic lead sulphates optionally combined with at least one neutral or dibasic lead stearate.

According to this second variant, the composition comprises a content of scavenger of the organic type based on lead of between 1 and 10 g per 100 g of halogenated polymer.

In accordance with a specific embodiment of this second variant, the composition comprises, in addition, at least one scavenger of the organic type chosen from the calcium salts of carboxylic acids described above.

According to a specific embodiment, the content of scavenger of the organic type mentioned above is betwseen 0.1 and 3 g per 100 g of halogenated polymer.

A third variant consists of a composition comprising, in addition to zinc acetylacetonate monohydrate, at least one organic scavenger chosen from tin salts.

All the tin-based compounds described above may be chosen as constituent elements of the composition according to this third variant.

More particularly, the stabilizing composition has a content of scavenger of the organic type mentioned above of between 0.1 and 3 g per 100 g of halogenated polymer, preferably of between 0.2 and 2 g in relation to the same reference. According to a more specific embodiment of this variant, the content of scavenger based on tin is between 0.3 and 1 g per 100 g of halogenated polymer.

The formulations according to the invention may also comprise, if necessary, at least one free β-diketone.

More particularly, the β-diketones are chosen from compounds corresponding to the formula (I) $R^1COCHR^2COR^3$, in which formula, $R^2$ and $R^3$, which are identical or different, represents a $C_1$–$C_{30}$ hydrocarbon radical and $R^2$ represents a hydrogen atom or a $C_1$–$C_4$ alkyl radical.

More particularly, the $R^1$ or $R^3$ radicals of the said β-diketone, which are identical or different, represent a linear or branched, $C_1$–$C_{24}$ alkyl or alkenyl radical; a $C_6$–$C_{30}$ aryl radical, substituted or otherwise with at least one alkyl radical and/or a halogen atom and/or a silicon atom; a $C_3$–$C_{14}$ cycloaliphatic radical and optionally capable of containing carbon-carbon double bonds.

More particularly, the $R^1$ and $R^3$ radicals represent a linear or branched $C_1$–$C_{18}$ alkyl radical; a $C_6$–$C_{10}$ aryl radical, substituted or otherwise with at least one alkyl radical and/or one halogen atom; or a cycloaliphatic radical as defined above.

The abovementioned radicals may be optionally modified by the presence, in the aliphatic chain, of one or more groups of formula —O—, —CO—O—, —CO—. Preferably, the radicals do not comprise such functions.

According to another variant, the $R^1$ and $R^3$ radicals may be linked to each other such that the β-diketone forms a ring.

The $R^2$ radical may be either a hydrogen atom, or a $C_1$–$C_4$ alkyl radical whose aliphatic chain may be interrupted by one or more groups of formula —O—, —CO—O—, —CO—.

Preferably, $R^2$ represents a hydrogen atom or a methyl radical.

By way of example of such compounds, there may be mentioned most particularly octanoylbenzoyl-methane, stearoylbenzoylmethane, dibenzoylmethane or acetylbenzoylmethane.

The content of free β-diketone is usually between 0.05 and 1 g per 100 g of halogenated polymer.

It should be noted that the formulation may even comprise a β-diketone in the form of a calcium, magnesium or zinc chelate (with the exception of zinc acetylacetonate).

In this case, the content of this compound is between 0.05 and 1 g per 100 g of halogenated polymer.

The formulation may, in addition, comprise at least one polyol comprising 2 to 32 carbon atoms and having two to nine hydroxyl groups.

Among these compounds, there may be mentioned $C_3$–$C_{30}$ diols such as propylene glycol, butanediol, hexanediol, dodecanediol, neopentyl glycol, polyols such as trimethylolpropane, pentaerythritol, dipentaerythritol, tripentaerythritol, xylitol, mannitol, sorbitol, glycerin, mixtures of oligomers of glycerin having a degree of polymerization of 2 to 10.

Another family of polyols which may be suitably used consists of the partially acetylated polyvinyl alcohols.

It is likewise possible to use hydroxylated compounds comprising isocyanurate groups, alone or in combination with the abovementioned polyols, such as for example tris(2-hydroxyethyl.)isocyanurate.

The quanity of polyol used is generally between 0.05 and 5 g per 100 g of halogenated polymer. More particularly, it is less than 2 g per 100 g of halogenated polymer.

It is possible, where appropriate, to incorporate into the composition according to the invention compounds of the type including organic phosphites, such as for example trialkyl, aryl, triaryl, dialkylaryl or diarylalkyl phosphites, for which the term alkyl designates hydrocarbon groups of $C_8$–$C_{22}$ polyols or monoalcohols, and the term aryl designates aromatic groups of phenol or of phenol substituted with $C_6$–$C_{12}$ alkyl groups. It is likewise possible to use calcium phosphites, such as for example compounds of the $Ca(HPO_3).(H_2O)$ type as well as phosphite-hydroxyaluminium-calcium complexes.

The content of additive of this type is usually between 0.1 and 2 g per 100 g of halogenated polymer.

The stabilizing compositions according to the invention may likewise comprise at least one synthetic, crystalline alkali metal aluminosilicate having a water content of between 13 and 25% by weight, having the composition $0.7–1M_2O.Al_2O_3.1.3–2.4SiO_2$ in which M represents an alkali metal such as in particular sodium. Zeolites of the NaA type, as described in U.S. Pat. No. 4,590,233, are in particular suitable.

The content of this type of compound varies generally between 0.1 and 5 g per 100 g of halogenated polymer.

The composition according to the invention may also comprise compounds of the type including epoxides. These compounds are generally chosen from epoxidized polyglycerides, or epoxidized fatty acid esters, such as epoxidized linseed, soya bean or fish oils.

The quantity of compounds of this type usually varies between 0.5 and 10 g per 100 g of halogenated polymer.

Other conventional additives in the field may be incorporated, if necessary, into the formulations stabilized according to the process of the invention.

Thus, the formulation may comprise white or coloured pigments.

By way of example of coloured pigments, there may be mentioned rare-earth-based compounds such as in particular cerium sulphide.

According to a specific variant of the invention, the composition comprises a white pigment which is most often titanium dioxide.

More particularly, the titanium dioxide is chosen in rutile form. The size of the titanium dioxide particles is generally between 0.1 and 0.5 µm.

According to a specific embodiment of the invention, titanium dioxide is used in the form of rutile having been subjected to a surface treatment, preferably mineral.

Among the suitable titanium dioxides, there may be mentioned with no limitation being intended, the titanium dioxide Rhoditan RL18 marketed by Millenium, the titanium dioxides Kronos 2081 and 2220 marketed by Kronos.

The quantity of pigment introduced into the formulation comprising the polymer varies within wide limits and depends on the colouring power of the pigment and on the desired final colour. However, by way of example, the quantity of pigment may vary from 0.5 to 15 g per 100 g of chlorinated polymer.

In the particular case of titanium dioxide, the content may be more particularly between 0.1 and 20 g per 100 g of halogenated polymer, preferably between 2 and 15 g in relation to the same reference.

Other conventional additives may supplement the formulation, depending on the application for which it is intended.

As a general rule, the formulation may comprise phenolic antioxidants, anti-UV agents such as 2-hydroxybenzophenones, 2-hydroxybenzotriazoles or sterically hindered amines, usually known by the term Hals.

The content of this type of additive generally varies between 0.05 and 3 g per 100 g of resin.

If necessary, it is possible to use lubricants which will facilitate the procedure, chosen in particular from glycerol monostearates or propylene glycol, fatty acids or esters thereof, montanate waxes, polyethylene waxes or oxidized derivatives thereof, paraffins, metal soaps, functionalized polymethylsiloxane oils such as for example γ-hydroxypropylenated oils.

The quantity of lubricant entering into the halogenated polymer-based formulation varies in general between 0.05 and 2 g per 100 g of resin.

The formulation may also comprise plasticizers chosen from alkyl phthalates. The compounds most generally used are chosen from di(2 ethylhexyl) phthalate, esters of linear $C_6$–$C_{12}$ diacids, trimellitates or phosphate esters.

The quantity of plasticizing agent used in the formulations varies in a broad range depending on the rigid or flexible character of the final polymer. As a guide, the content varies from 5 to 100 g per 100 g of halogenated polymer.

The preparation of the formulations may be carried out by any means known to persons skilled in the art.

The conventional methods of incorporation are perfectly suitable for producing the formulation based on PVC.

Thus, it is possible to carry out this operation in a mixer provided with a paddle and counter-paddle system operating at a high speed.

Generally, a temperature at which the constituents of the formulation are incorporated is less than 130° C.

Once the mixture has been prepared, the composition is formed according to the usual methods in the field such as injection, extrusion-blowing, extrusion, calendering or moulding by rotation.

The temperature at which the forming is carried out varies in general from 150 to 220° C.

Concrete but nonlimiting examples will now be presented.

EXAMPLE 1

224.2 g of zinc oxide and 300 g of solvent (acetonitrile/methanol mixture) are introduced into a turbosphere reactor. The mixture is heated to reflux temperature and 600 g of acetylacetone are added over a period of 1 hour while the reaction mixture is maintained under reflux. The mixture is maintained under reflux for an additional 1 hour and then the solvent is distilled under atmospheric pressure. When the solvent no longer distils, the mixture is placed under a vacuum of 200 torr for 10 minutes.

802 g of zinc acetylacetonate are recovered (water content 5.5%)

EXAMPLE 2

The procedure is carried out as in Example 1 except for the fact that the solvent consists of 300 g of methanol. Furthermore, the refluxing time following the introduction of the reagents is 2 hours.

793 g of zinc acetylacetonate are recovered (water content 5.1%)

EXAMPLE 3

The procedure is carried out as in Example 1 except for the fact that the solvent consists of 300 g of 90% ethanol (the remainder being water).

801 g of zinc acetylacetonate are recovered (water content 6.3%).

What is claimed is:

1. A method for stabilizing a halogenated polymer comprising incorporating in said halogenated polymer a stabilizing effective amount of zinc acetylacetonate hydrate, wherein said zinc acetylacetonate hydrate comprises between 4.4% and 8.8% by weight of water.

2. The method according to claim 1, wherein the zinc acetylacetonate has the following average formula:

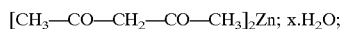

in which x is a number which is an integer or otherwise, greater than or equal to 0.65.

3. The method according to claim 2, wherein the coefficient x is between 0.65 and 1.3.

4. The method according to claim 3, wherein the coefficient x is between 0.7 and 1.2.

5. A process for the preparation of zinc acetylacetonate hydrate, wherein said zinc acetylacetonate hydrate comprises between 4.4% and 8.8% by weight of water, comprising contacting and reacting a zinc oxide and/or hydroxide with acetylacetonate, in the presence of a solvent, wherein the quantity of solvent is between 20 and 200 parts by weight, per 100 parts by weight of acetylacetonate.

6. The process according to claim 5 wherein the solvent is removed at the end of the reaction.

7. The process according to claim 5, wherein the solvent comprises compounds which are inert under the reaction conditions and whose boiling temperature is at most 100° C., measured at atmospheric pressure.

8. The process according to claim 5, wherein the contacting is carried out by introducing the acetylacetone into a zinc oxide and/or hydroxide and solvent mixture.

9. The process according to claim 8, wherein the contacting is carried out at a temperature of less than or equal to the reflux temperature of the solvent.

10. The process according to claim 5, wherein the quantity of solvent is between 20 and 100 parts by weight per 100 parts by weight of acetylacetone.

11. The process according to claim 10, wherein the quantity of solvent is between 40 and 100 parts by weight per 100 parts by weight of acetylacetone.

* * * * *